(12) United States Patent
DeLisle

(10) Patent No.: US 11,696,859 B2
(45) Date of Patent: Jul. 11, 2023

(54) WALL-MOUNTED MEDICAL KIT

(71) Applicant: Joshua J. DeLisle, Hanover, MA (US)

(72) Inventor: Joshua J. DeLisle, Hanover, MA (US)

( * ) Notice: Subject to any disclaimer, the term of this patent is extended or adjusted under 35 U.S.C. 154(b) by 118 days.

(21) Appl. No.: 17/149,526

(22) Filed: Jan. 14, 2021

(65) Prior Publication Data

US 2021/0212869 A1 Jul. 15, 2021

Related U.S. Application Data

(60) Provisional application No. 62/961,066, filed on Jan. 14, 2020.

(51) Int. Cl.

| | |
|---|---|
| *A61F 17/00* | (2006.01) |
| *B65D 33/00* | (2006.01) |
| *B65D 33/14* | (2006.01) |
| *B65D 27/06* | (2006.01) |
| *B65D 27/20* | (2006.01) |
| *B65D 33/24* | (2006.01) |

(52) U.S. Cl.
CPC .............. *A61F 17/00* (2013.01); *B65D 27/06* (2013.01); *B65D 27/20* (2013.01); *B65D 33/004* (2013.01); *B65D 33/14* (2013.01); *B65D 33/24* (2013.01); *B65D 2203/02* (2013.01); *B65D 2313/02* (2013.01)

(58) Field of Classification Search
CPC ......... A61F 17/00; B65D 27/06; B65D 27/20; B65D 33/004; B65D 33/14; B65D 33/24; B65D 2203/02; B65D 2313/02

USPC .......................................................... 206/570
See application file for complete search history.

(56) References Cited

U.S. PATENT DOCUMENTS

| | | | | |
|---|---|---|---|---|
| 4,441,639 A | * | 4/1984 | Craw ..................... | B64D 17/40 |
| | | | | 224/237 |
| 2005/0136760 A1 | * | 6/2005 | Anderson ............... | B32B 15/20 |
| | | | | 442/131 |
| 2011/0017633 A1 | * | 1/2011 | Holstein .................. | A61F 17/00 |
| | | | | 206/570 |
| 2021/0236354 A1 | * | 8/2021 | Cragg ..................... | A61F 17/00 |

FOREIGN PATENT DOCUMENTS

| | | | | |
|---|---|---|---|---|
| DE | 102018109741 A1 | * | 10/2019 | ........... A61F 15/001 |
| EP | 0730853 A2 | * | 9/1996 | |

OTHER PUBLICATIONS

Machine translation of DE-102018109741-A1.*
Machine translation of EP-0730853-A2.*

* cited by examiner

*Primary Examiner* — Jes F Pascua
(74) *Attorney, Agent, or Firm* — Prince Lobel Tye LLP

(57) ABSTRACT

A wall-mounted drug overdose response kit with a wall-mounted carrier and a pouch that is configured to hold at least one dose of a drug that needs to be accessed by first responders, wherein the pouch is configured to be held by the carrier such that the pouch can be easily removed from the carrier.

7 Claims, 4 Drawing Sheets

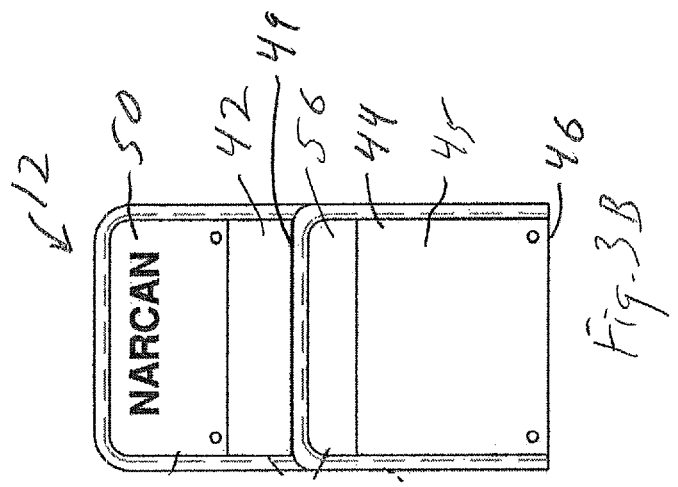
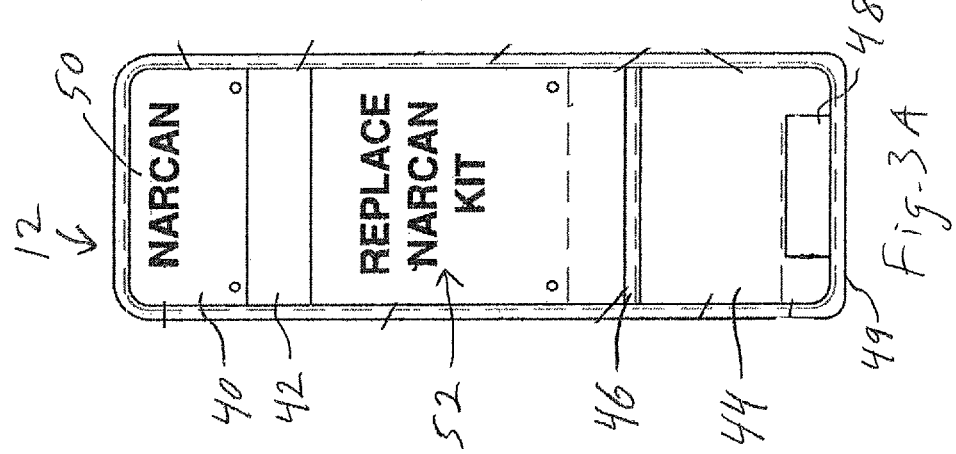

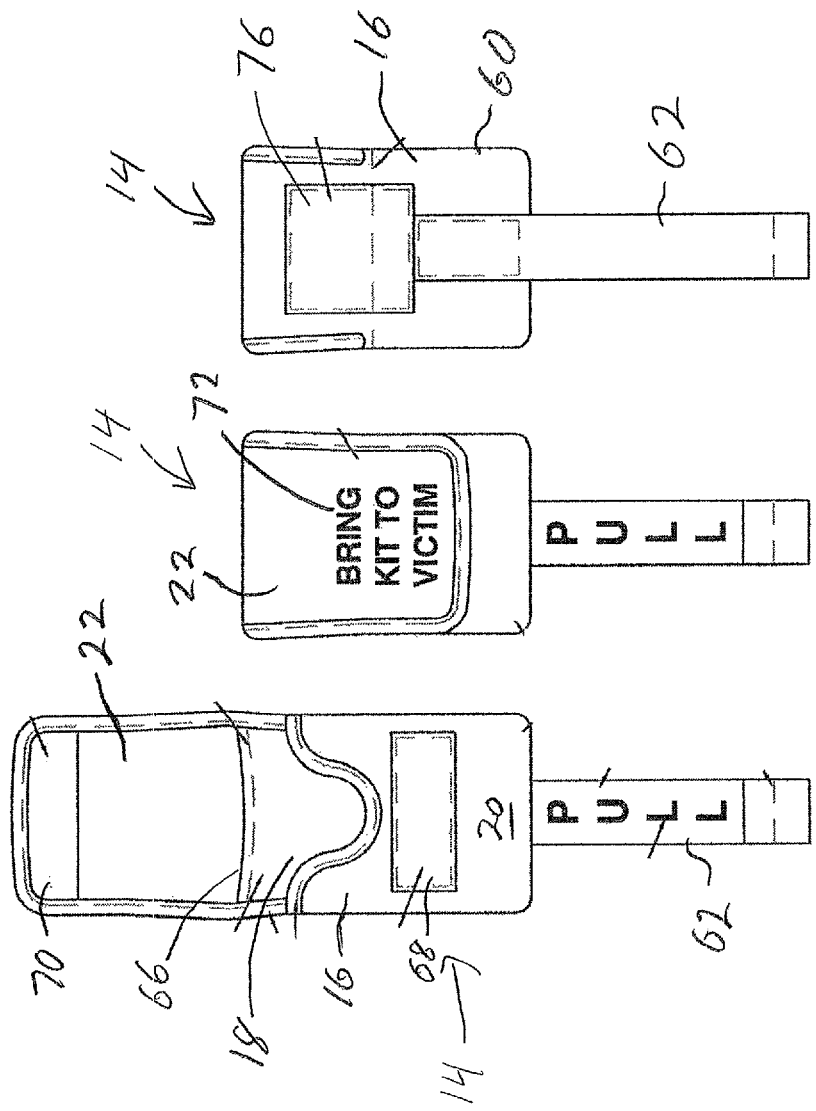

WALL-MOUNTED MEDICAL KIT

CROSS-REFERENCE TO RELATED APPLICATION

This application claims priority of Provisional Patent Application 62/961,066 filed on Jan. 14, 2020, the disclosure of which is incorporated herein by reference.

BACKGROUND

Drug overdoses can be treated/reversed by the application of a drug such as NARCAN. The drug should be easily and quickly available to any first responder. NARCAN comes in a small nasal applicator which may be contained within a blister pack in order to maintain sterility and protect the vial. NARCAN can be administered using the above mentioned nasal applicator/atomizer or a medicine atomizer/applicator. First responders thus need access to one or more doses of NARCAN (and/or other medicines) and related equipment and supplies such as gloves and a face shield. For quick access to the medication in case of an unexpected overdose, it would be helpful to have the drug easily and quickly accessible.

SUMMARY

Featured in this disclosure is a wall-mounted drug overdose response kit. The kit comprises a back plate that can be mounted to a wall, and a pouch that is removably coupled to the back plate and includes a pull strap so the pouch can be quickly and easily removed from the back plate. The pouch contains the drug and may also contain any related equipment and supplies such as gloves and a face shield. Preferably but not necessarily the pouch is removably coupled to the back plate with a hook and loop-type fastener system that can be released with a simple tug. In an example the pouch includes on its outside text that labels it as including supplies that need to be brought to the overdose victim. In an example the back plate includes text that is revealed only when the pouch has been removed, and serves as a reminder to the user to replace any supplies that were used before the pouch is re-coupled to the back plate.

In an aspect, a wall-mounted drug overdose response kit includes a wall-mounted carrier and a pouch that is configured to hold at least one dose of a drug that needs to be accessed by first responders, wherein the pouch is configured to be held by the carrier such that the pouch can be easily removed from the carrier.

Some examples include the above and any of the below. In an example the pouch comprises a projecting strap, so that the pouch can be removed from the carrier with a tug on the strap. In an example the carrier is clearly marked with the one or more words that identify the drug contents of the pouch. In an example the carrier can be installed by attaching the hard back to a surface with screws or by using adhesive. In an example across the front of the assembled wall mount are two strips of Velcro® hook and loop fastener system, one strip is on the front and the other is on the back, at the bottom. In an example the bottom is folded up so the two strips are adjacent at the front side. In an example the pouch has Velcro® hook and loop fastener system on the back that mates with both Velcro® hook and loop fastener system strips of the wall mount. In an example when the strap is pulled the pouch is pulled off the wall mount, and the flap of the wall mount then falls down to reveal instructions to replace the drug. In an example the pouch has an interior that is sized and shaped to hold at least one dose of a drug, at least one pair of gloves, and at least one face shield. In an example the response kit is marked with instructions to bring the kit to the victim and comprises a clearly marked pull strap.

BRIEF DESCRIPTION OF THE DRAWINGS

FIG. 3A is a front open view of a back plate for a wall-mounted medical kit,
and FIG. 3B is a closed view thereof.
FIG. 4A is a front open view of a medical kit,
FIG. 4B is a closed view thereof,
and FIG. 4C is a rear view of the kit of FIG. 4B.

DETAILED DESCRIPTION

The wall-mounted drug overdose response kit of one embodiment is made of weather resistant insulated material and consists of two parts—a wall mounted carrier and a pouch that can be removably coupled to the carrier. The wall mounted carrier is clearly marked near the top with the word(s) (e.g., "NARCAN" or "ODKIT") to identify the contents of the response pouch that it carries. The wall mount can be installed by attaching the hard back to a surface with screws, or by using adhesive. Across the front of the assembled wall mount are two strips of Velcro® hook and loop fastener system. One strip is on the front and the other is on the back, at the bottom. The bottom is folded up so the two strips are adjacent. The pouch has Velcro® hook and loop fastener system on the back that mates with both strips of the wall mount. The pouch has an extending pull strap. When the strap is pulled the pouch is pulled off the wall mount. The flap of the wall mount then falls down, to reveal the instructions (e.g., "replace Narcan kit") that are covered when the bottom is folded up. In an example the response kit is purpose built to hold two doses of NARCAN, one pair of gloves, and one face shield. The response kit can be marked with instructions to bring the kit to the victim, and designed with a clearly marked pull strap.

Steps for operation: mount wall mount to wall; lift "replace kit" flap; secure flap to wall mount with response kit; pull response kit off wall using pull strap and bring to overdose victim; "replace kit" flap drops to indicate kit needs to be replaced; bring kit to victim and attempt resuscitation; refill kit and replace it on wall mount so it is ready for next time.

Figure 1:
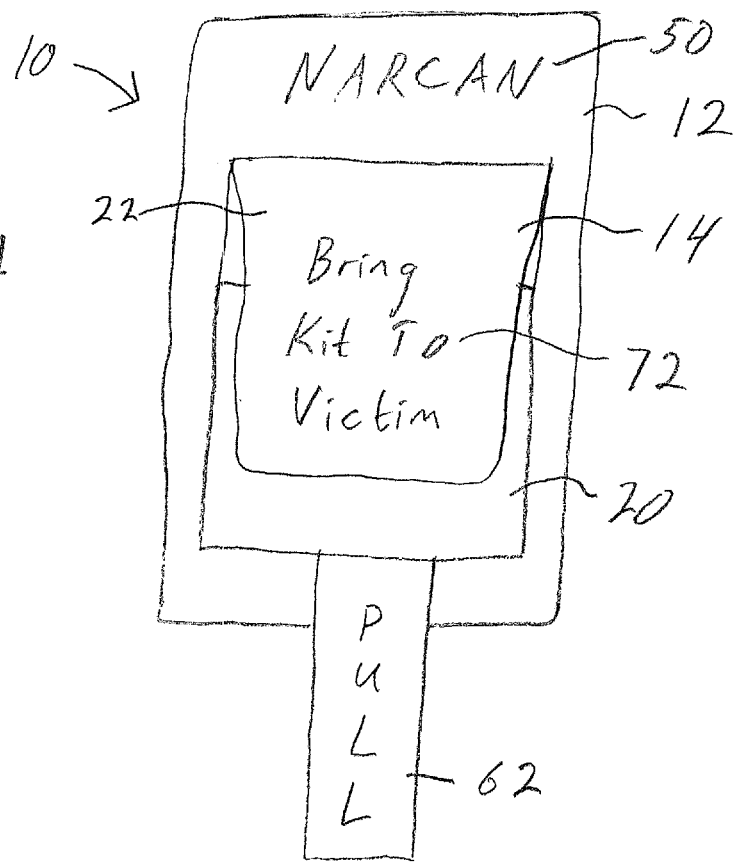
FIG. 1 is a front view of a wall-mounted medical kit.

Assembled wall-mounted overdose response kit 10 is shown in FIG. 1. Wall-mounted carrier 12 removably carries pouch 14 that is configured to hold at least one dose of a drug that needs to be accessed by first responders or other medical or emergency personnel. The pouch is configured to be held by the carrier such that the pouch can be easily removed from the carrier by pulling on strap 62. Carrier 12 includes text (e.g., "NARCAN") that identifies the drug inside the pouch. Pouch 14 has flap 22 that folds over the container portion 20 that carries at least the identified drug. Note that the drug can be used for overdoses, or other emergency use drugs could be carried and identified by text 50. The visible front of flap 14 also carries instructions for the user, such as "bring kit to victim" or the like. In an example carrier 12 can be installed by attaching the hard back to a surface with screws or by using adhesive.

Figure 2:
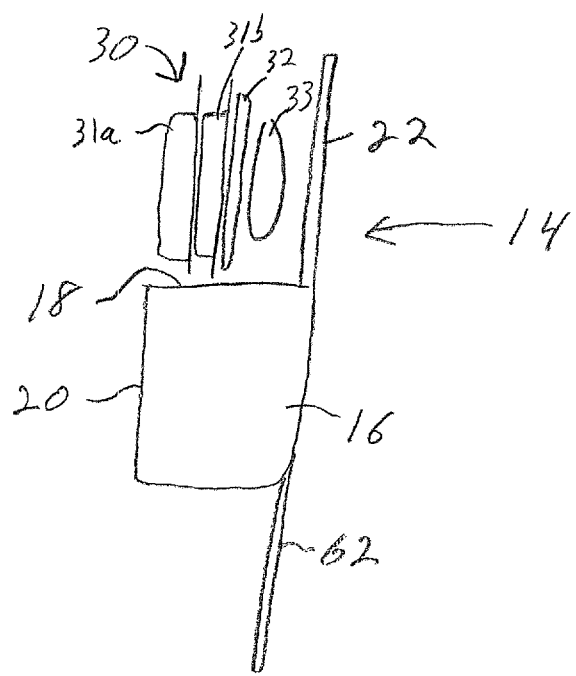
FIG. 2 is a side view of a wall-mounted medical kit being prepared.
Figure 8:
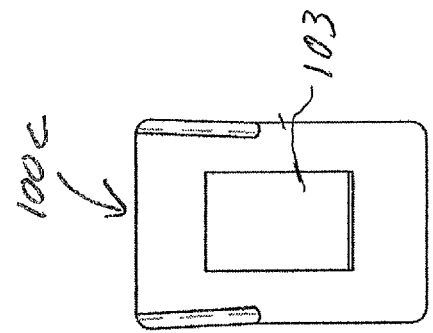
FIG. 8 is a rear view of an alternative medical kit.
Figure 7:
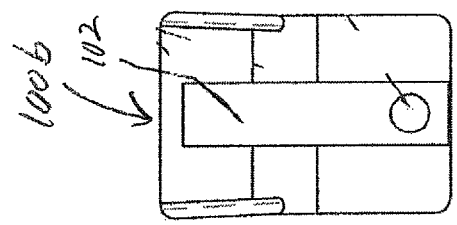
FIG. 7 is a rear view of an alternative medical kit.
Figure 6:
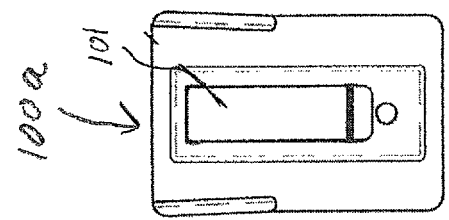
FIG. 6 is a rear view of an alternative medical kit.

FIG. 2 illustrates pouch 14 open and being loaded with supplies through open top 18 of pouch container 16 with front 20. In this non-limiting example the supplies include one or two doses of the drug (dose packs 31a and 31b illustrated), a pair of disposable gloves 32, and a face shield 33. Flap 22 is folded down over front 20 and is removably closed thereto, as explained below. Strap 62 is permanently connected to the container 16.

FIGS. 3A and 3B illustrate wall-mounted carrier 12 that comprises a plate 40 that can be fixed to a wall through any conventional means such as screws or adhesive. Velcro® hook and loop fastener system strip 42 is located across the width, near the top. Lower flap 44 can fold up along seam 46 such that bottom edge 49 is just below Velcro® hook and loop fastener system strip 42. The rear side 45 of flap 44 carries, adjacent to lower edge 49, another Velcro® hook and loop fastener system strip 56. Strips 42 and 56 are both of the same type of hook and loop-style fastener, e.g., they are both the loop side of the fastener system. Words 50 near the top are always visible, while words 52 near the middle are covered by flap 44.

Pouch 14, FIGS. 4A-4C, has container 16 with open top 18. Flap 22 has Velcro® hook and loop fastener system strip 70 such that when flap 22 is folded down along seam 66 Velcro® hook and loop fastener system strip 70 matches with Velcro® hook and loop fastener system strip 68; strips 68 and 70 are mating portions of hook and loop fasteners, so that the flap is removably held down to keep the container closed. Words 72 are printed on the flap 22 such that they are visible when the flap is folded down. Rear side 60 of container 16 includes Velcro® hook and loop fastener system patch 76 that is configured to couple to both of strips 42 and 56 of carrier 12, so that the pouch is removably held on the carrier.

More generally, in an example across the front of the assembled wall mount are two strips of Velcro® hook and loop fastener system, one strip is on the front and the other is on the back, at the bottom. In an example the bottom is folded up so the two strips are adjacent. In an example the pouch has Velcro® hook and loop fastener system on the back that mates with both Velcro® hook and loop fastener system strips of the wall mount. In an example when the strap is pulled the pouch is pulled off the wall mount, and the flap of the wall mount then falls down to reveal instructions to replace the drug. In an example the pouch has an interior that is sized and shaped to hold at least one dose of a drug, at least one pair of gloves, and at least one face shield. In an example the response kit is marked with instructions to bring the kit to the victim and comprises a clearly marked pull strap.

Figure 5B:
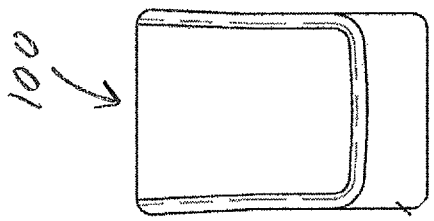
FIG. 5A is a front open view of a medical kit and FIG. 5B is a closed view thereof.
Figure 5A:
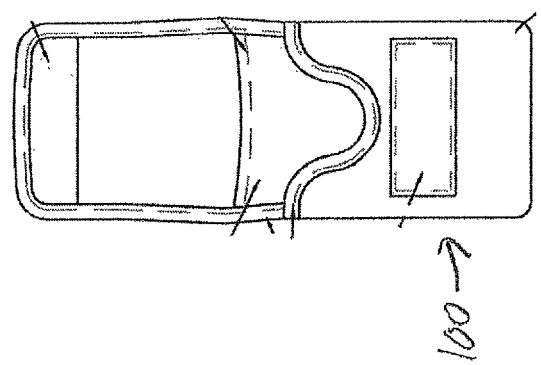

Alternative examples of the pouch are shown in FIGS. 5A, 5B, 6, 7, and 8. The overall construction is much like the response kit pouch of the first embodiment, as shown in FIGS. 5A and 5B, where there is no strap so that pouch 100 can be carried on another structure such as a belt that has a receiving Velcro® hook and loop fastener system patch. Other differences are on the backs of the pouches, and provide for different mounting and/or carrying options—a clip 101 in FIG. 6, a molle attachment with snap 102 in FIG. 7, and a Velcro® hook and loop fastener system strap 103 in FIG. 8. These can be belt carry options or an option to be clipped or attached to something stationary.

In summary, the wall-mounted drug response kit has a wall-mounted carrier (back plate) and a pouch that is configured to hold at least one dose of a drug that needs to be accessed by medical or emergency personnel, including first responders (such as Narcan). The pouch is held by the carrier such that it can be easily removed, for example with a simple tug on a part of the pouch (such as a projecting strap).

A number of implementations have been described. Nevertheless, it will be understood that additional modifications may be made without departing from the scope of the inventive concepts described herein, and, accordingly, other examples are within the scope of the following claims.

What is claimed is:

1. A wall-mounted drug overdose response kit, comprising:
   a) a carrier that is configured to be mounted to a surface, the carrier comprising:
      a generally planar body portion with a hard back that can be coupled to the surface with screws or by using adhesive and an opposed front that comprises a first area of a first part of a two-part hook and loop fastener system proximate a top end of the body portion;
      a flexible lower flap depending from the body portion and defining a lower end, the lower flap having a front side, an opposed rear side, and a second area of the first part of a two-part hook and loop fastener system on the rear side of the flap proximate the lower end; and
      a seam between the lower flap and the body portion;
      wherein the lower flap is configured such that the lower end can be lifted from an empty position wherein the second area of the first part of the two-part hook and loop fastener system is farthest from the first area of the first part of the two-part hook and loop fastener system, into a use position by folding along the seam such that the second area of the first part of the two-part hook and loop fastener system is adjacent to the first area of the first part of the two-part hook and loop fastener system; and
   b) a pouch that is configured to hold at least one dose of a drug that needs to be accessed by first responders, the pouch comprising:
      a pouch container with a top, bottom, front, and rear, and an open top, wherein the pouch container has an interior that is sized and shaped to hold at least one dose of the drug;
      a depending pouch flap that is coupled to the rear of the pouch container proximate the top, has a rear surface, and is configured to be folded down to cover the open top of the pouch container and to cover part of the front of the pouch container;
      a first area of a second part of the two-part hook and loop fastener system on the rear of the pouch container, wherein the first area of a second part of the two-part hook and loop fastener system is configured to be coupled to the first and second areas of the first part of the two-part hook and loop fastener system of the carrier, to removably hold the pouch on the carrier; and
      a pull strap that is coupled to the rear of the pouch container proximate the bottom and extends below the bottom of the pouch container, wherein the pull strap is configured to be pulled downward by a user to separate the first and second parts of the two-part hook and loop fastener system, to remove the pouch from the carrier;

wherein when the pouch is removed from the carrier the lower flap of the carrier is pulled down and folds along the seam to the empty position.

2. The wall-mounted drug overdose response kit of claim 1, wherein the front of the body portion of the carrier, above the first area of the first part of a two-part hook and loop fastener system, is marked with the one or more words that identify the drug contents of the pouch.

3. The wall-mounted drug overdose response kit of claim 2, wherein the front of the body portion of the carrier, below the first area of the first part of a two-part hook and loop fastener system, is marked with the one or more words that identify the drug contents of the pouch.

4. The wall-mounted drug overdose response kit of claim 3, wherein the one or more words that identify the drug contents of the pouch are covered by the flap when the flap is in the use position and are not covered by the flap when the flap is in the empty position.

5. The wall-mounted drug overdose response kit of claim 1, wherein the rear of the pouch flap is marked with instructions to bring the kit to the victim.

6. The wall-mounted drug overdose response kit of claim 1, wherein the pouch is further configured to hold a pair of disposable gloves.

7. The wall-mounted drug overdose response kit of claim 6, wherein the pouch is further configured to hold a face shield.

* * * * *